United States Patent [19]

Philipp et al.

[11] 4,232,029

[45] Nov. 4, 1980

[54] 1-HYDROXYIMIDAZOLE-5-METHANAMINE DERIVATIVES

[75] Inventors: Adolf H. Philipp, St. Laurent; Ivo L. Jirkovsky, Montreal, both of Canada

[73] Assignee: American Home Products Corporation, New York, N.Y.

[21] Appl. No.: 957,627

[22] Filed: Nov. 3, 1978

[51] Int. Cl.$^3$ .................. A61K 31/415; A61K 31/44; C07D 233/70; C07D 403/02
[52] U.S. Cl. ............................... 424/263; 424/273 R; 546/210; 548/337; 548/342
[58] Field of Search ..................... 548/336, 337, 342; 546/210; 424/263, 273 R

[56] References Cited

U.S. PATENT DOCUMENTS 3,488,423  1/1970  Doebel et al. ..................... 548/337

OTHER PUBLICATIONS

Franchetti et al., Il Farmaco, Ed. Sci., vol. 27, pp. 46 to 59, (1972).
Chemical Abstracts, Ninth Collective Index, vols. 76–85, of 1972–1976, p. 19367CS.
Chemical Abstracts, vol. 84, Abst. 90447n, (1976), Abst. of Kitaura et al., Bioorganic Chemistry, vol. 4, pp. 327–349, 1975).
Kitaura et al., Bioorganic Chemistry, vol. 4, pp. 327–349, 1975.

*Primary Examiner*—John D. Randolph
*Attorney, Agent, or Firm*—Arthur E. Wilfond

[57] ABSTRACT

1-Hydroxyimidazole-5-methanamine derivatives characterized by having a lower alkyl group at positions N, N and 5 of the latter derivatives as well as having various substituents at position 2 of the imidazole ring are disclosed. These derivatives are useful as antihypertensive agents in a mammal. Methods for their preparation, use and pharmaceutical compositions also are disclosed.

27 Claims, No Drawings

1-HYDROXYIMIDAZOLE-5-METHANAMINE DERIVATIVES

BACKGROUND OF THE INVENTION (a) Field of the Invention

This invention relates to novel 1-hydroxyimidazole-5-methanamine derivatives, to therapeutically acceptable acid addition salts thereof, to processes for their preparation and to pharmaceutical compositions.

More specifically, the present invention relates to novel N,N,5-tri(lower alkyl)-1-hydroxyimidazole-5-methanamine derivatives which are further substituted at position 2 of the imidazole ring. The derivatives are antihypertensive agents.

(b) Description of the Prior Art

A number of imidazole-5-methanamines have been reported. For example, 2-isopropyl-4-propyl-5-(dimethylaminomethyl)imidazole is reported by M. Masui et al., Chem. Pharm. Bull., 21, 1387 (1973) and a rather large number of variously substituted N,N-di(lower alkyl)imidazole-5-methanamine derivatives are reported by G. J. Durant et al., British Pat. No. 1,341,375, published Dec. 19, 1973 to have histamine like properties or to antagonize the action of histamine.

An article by P. Franchetti et al., Farmaco, Ed. Sci., 27, 46 (1972) discloses N,N-di(lower alkyl)-1-hydroxyimidazole-5-methamine-3-oxide derivatives useful for the reactivation of phosphorylated acetylcholinesterase.

SUMMARY OF THE INVENTION

The compounds of this invention are represented by formula I

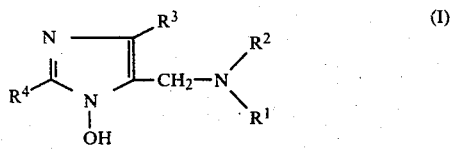

in which $R^1$, $R^2$ and $R^3$ each is lower alkyl, or $R^1$ is lower alkyl and $R^2$ and $R^3$ together form a chain of formula —C(=NOH)—CH$_2$— wherein the —CH$_2$— is joined to the nitrogen, and $R^4$ is lower alkyl, 1-naphthalenyl, 2-, 3- or 4-pyridinyl, 2- or 3-furyl, 2- or 3-thienyl, phenyl or phenyl mono-, di- or trisubstituted with halo, lower alkyl, lower alkoxy, hydroxy or trifluoromethyl.

A preferred group of compounds are represented by formula I in which $R^1$, $R^2$ and $R^3$ each is lower alkyl, or $R^1$ is lower alkyl and $R^2$ and $R^3$ together form a chain of formula —C(=NOH)—CH$_2$— wherein the —CH$_2$— is joined to the nitrogen, and $R^4$ is lower alkyl, 1-naphthalenyl, 2-pyridinyl, 2-furyl, 3-thienyl, phenyl or phenyl mono- or disubstituted with halo, lower alkyl or hydroxy.

A most preferred group of compounds are represented by formula I in which $R^1$, $R^2$ and $R^3$ each is lower alkyl, or $R^1$ is lower alkyl and $R^2$ and $R^3$ together form a chain of formula —C(=NOH)—CH$_2$— wherein the —CH$_2$— is joined to the nitrogen, and $R^4$ is 3-thienyl, phenyl or phenyl mono- or disubstituted with halo or lower alkyl.

The compounds of formula I are prepared by a process, which comprises condensing a compound of formula II,

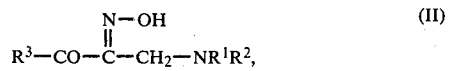

in which $R^1$, $R^2$ and $R^3$ are as defined herein with an aldehyde of formula $R^4$—CHO in which $R^4$ is as defined herein in the presence of ammonium hydroxide.

The therapeutically acceptable acid addition salts of the compounds of formula I are included within the scope of this invention.

The compounds of this invention are useful for treating hypertension in a mammal by administering to the mammal an effective antihypertensive amount of a compound of formula I or a therapeutically acceptable acid addition salt thereof.

The compounds of this invention form a pharmaceutical composition which comprises a compund of formula I, or a therapeutically acceptable acid addition salt thereof, and a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkanol" as used herein means both straight and branched chain alkanols containing from one to four carbon atoms and includes methanol, ethanol, isopropanol, butanol and the like.

Also included in this invention are the possible stereochemical isomers of the compounds of formula I. Such isomers can be obtained in substantially pure form by classical separation techniques and by sterically controlled synthesis. Individual enantiomers, which might be separated by fractional crystallization of the diastereomeric salts thereof, are also included.

The term "therapeutically acceptable addition salt" as used herein includes the therapeutically acceptable acid addition salts of the compound of formula I. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding base. For many purposes it is preferable to administer the salts rather than the base compounds. Suitable acids to form these salts include the common mineral acids, for instance, hydrobromic, hydrochloric, sulfuric or phosphoric acid; as well as the organic acids, for instance, formic, acetic, maleic, fumaric, citric, or tartaric acid; or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or therapeutically acceptable acid addition salts thereof is demonstrated in standard pharmacological tests, for example, in tests conducted in the spontaneously hypertensive rat such as described by I. Vavra, et al., Can. J. Physiol. Pharmacol., 51 727 (1973). More specifically exemplified, the compounds of formula I are shown to be effective antihypertensive agents by using the testing method described in this publication. The latter test method is modified so that the test compound is administered to the rat by gastric gavage and the systolic blood pressure is measured by the tailcuff method before administration of the compound and 4 hours thereafter. Using this method, the following representative compounds of formula I are effective for reducing the systolic blood pressure (BP) in the spontaneously hypertensive rat (the amount of test compound and its reduction in BP is indicated in the parentheses): 1-hydroxy-N,N,4-trimethyl-2-(4-methylphenyl)-1H-imidazole-5-methanamine dihydrochloride (described in Example 2, at a dose of 25 mg/kg of body weight causes 8 to 12% reduction in BP), 2-(4-fluorophenyl)-1-hydroxy-N,N,4-trimethyl-1H-imidazole-5-methanamine dihydrochloride (described in Example 2, at a dose of 25 mg/kg of body weight causes a 8 to 12% reduction in BP), 2-(3-chlorophenyl)-1-hydroxy-N,N,4-trimethyl-1H-imidazole-5-methanamine dihydrochloride (described in Example 2, at a dose of 25 mg/kg of body weight causes a 15 to 20% reduction in BP), 2-(3,4-dichlorophenyl)-1-hydroxy-N,N,4-trimethyl-1H-imidazole-5-methanamine dihydrochloride (described in Example 2, at a dose of 50 mg/kg of body weight causes a 8 to 12% reduction in BP), 1-hydroxy-N,N,4-trimethyl-2-(3-thienyl)-1H-imidazole-5-methanamine dihydrochloride (described in Example 2, at a dose of 50 mg/kg of body weight causes a 8 to 12% reduction in BP), 2-(4-chlorophenyl)-1-hydroxy-N,N,4-trimethyl-1H-imidazole-5-methanamine dihydrochloride (described in Example 2, at a dose of 25 mg/kg of body weight causes a 15 to 20% reduction in BP) and 6,7-dihydro-1-hydroxy-6-methyl-2-phenyl-1H-imidazo[4,5-c]pyridine4[5H]-one, oxime dihydrochloride (described in Example 4, at a dose of 25 mg/kg of body weight causes a 8 to 12% reduction in BP).

When the compounds of formula I are used as antihypertensive agents in mammals, e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example enough saline or glucose to make the solution isotonic.

The tablet compositions contain the active ingredient in admixture with nontoxic pharmaceutical excipients are, for example, starch, milk, sugar, certain types of clay and so forth. The tablets can be uncoated or they can be coated by known techniques so as to delay disintegration and adsorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more colouring agents, one or more flavouring agents and one or more sweetening agents.

Non-aqueous suspensions can be formulated by suspending the active ingredient in a vegetable oil, for example, arachic oil, olive oil, sesame oil, or coconut oil, or in a mineral oil, for example, liquid paraffin, and the suspension may contain a thickening agent, for example, beeswax, hard paraffin or cetyl alcohol. These compositions can also contain a sweetening agent, flavouring agent or antioxidant.

The dosage of the compounds of formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilogram of body weight per day, although as aforementioned, variations will occur. However, a dosage level that is in the range from about 5.0 mg to about 100 mg per kilogram body weight per day is employed most desirably in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamterene and furosemide. Examples of still other suitable antihypertensive agents are prazosin, hydralazine and centrally active antihypertensive agents such as methyldopa, clonidine, and reserpine; as well as the β-adrenergic blocking agents, for instance, propanolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing diuretic agents and the β-adrenergic blocking agents. A combination of the foregoing antihypertensive and/or diuretic agents, e.g. propanolol and hydrochlorothiazide, can be substituted for a single agent. Suitable methods of administration, compositions and dosages of the above described diuretic and/or antihypertensive agents are described in medical textbooks; for instance, "Physicians' Desk Reference", 32 ed., Medical Economics Co., Oradell, N.J., U.S.A. 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt, is administered as described previously.

PROCESS

For the preparation of the compounds of formula I, one of the preferred starting materials are the compounds of formula II

in which $R^1$, $R^2$ and $R^3$ are as defined herein. The compounds of formula II are either known or can be prepared by utilizing described methods. For example, 1-diethylamino-2-hydroxyimino-3-butanone is described by G. B. Bachman and D. E. Welton, J. Org. Chem., 12, 221 (1947) and 3,5-dihydroxyimino-1-methyl-4-piperidinone is described by G. H. Cookson, J. Chem. Soc., 1328 (1953). By using the method described in the latter two references, other compounds of formula II are prepared readily. In this method, a ketoamine of formula $R^3$—CO—$CH_2CH_2NR^1R^2$ in which $R^1$, $R^2$ and $R^3$ are as defined herein is reacted with isopropyl nitrite and hydrogen chloride under anhydrous conditions at 25° to 40° C. for 0.5 to 5 hours and the corresponding compound of formula II is isolated.

Condensation of the compound of formula II with an aldehyde of formula $R^4$—CHO in which $R^4$ is as defined herein in the presence of ammonium hydroxide provides the corresponding compound of formula I

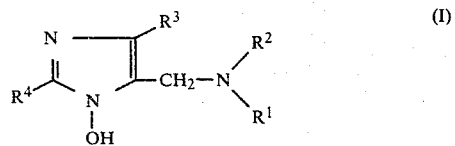

in which $R^1$, $R^2$, $R^3$ and $R^4$ are as defined herein. In this condensation about 1.0 to 2.0, preferably 1.05 to 1.4, molar equivalents of the aldehyde of formula $R^4$—CHO usually are used. The amount of ammonium hydroxide, in the form of 20 to 30% aqueous ammonium hydroxide, can vary from about 1.0 to 50 molar equivalents, however optimum results are usually obtained by using about 20 to 30 molar equivalents. In order to dissolve the starting materials, a water-miscible inert organic solvent is also present in the condensation reaction. A preferred solvent for this purpose can be selected from lower alkanols. Optimum yields of the compound of formula I are obtained by maintaining the condensation reaction at 20° to 30° C. for 15 to 30 hours. The compound of formula I is then isolated and purified by conventional methods, for example, evaporation, chromatography, crystallization and/or acid addition salt formation.

The following examples illustrate further this invention.

EXAMPLE 1

2-Hydroxyimino-1-Dimethylamino-3-Butanone Hydrochloride (II; $R^1$, $R^2$ and $R^3$=Me)

To a solution of 4-dimethylamino-2-butanone[34.5 g, 0.3 moles, described by E. C. du Feu et al., J. Chem. Soc., 56 (1937)] in dry isopropanol (120 ml), gaseous hydrogen chloride is introduced at 0° C. until the solution is acidic to congo red (ca. pH=4). Isopropanol saturated with hydrogen chloride (2 ml) is added. Isopropyl nitrite (29.4 g, 0.33 moles) is added dropwise with stirring while maintaining the reaction temperature at 30° to 35° C. After 30 min, diethyl ether (100 ml) is added and the mixture is stirred for 30 min. The precipitate is collected to obtain 47 g of the title compound, mp 188°–199° C. The latter precipitate is crystallized from ethanol-diethyl ether to obtain 32 g of title compound; mp 205°–206° C., nmr(DMSO-$d_6$) δ 2.4(s), 2.75(s), 4.07(s) and 12.35(broad singlet).

In the same manner but replacing 4-dimethylamino-2-butanone with an equivalent amount of a following compound of formula III: 4-diethylamino-2-butanone, 4-(N-methyl-N-pentylamino)-2-butanone, 1-dimethylamino-3-pentanone, 1-dipropylamino-5-methyl-3-heptanone or 1-(N-ethyl-N-propylamino)-3-octanone, the following compounds of formula II are obtained, respectively:

1-diethylamino-2-hydroxyimino-3-butanone hydrochloride, 2-hydroxyimino-1-(N-methyl-N-pentylamino)-3-butanone hydrochloride, 1-diethylamino-2-hydroxyimino-3-pentanone hydrochloride, 2-hydroxyimino-5-methyl-3-heptanone hydrochloride and 1-(N-ethyl-N-propylamino)-2-hydroxyimino-3-octanone hydrochloride.

EXAMPLE 2

1-Hydroxy-N,N,4-Trimethyl-2-(4-Methylphenyl)-1H-Imidazole-5-Methanamine (I; $R^1$, $R^2$ and $R^3$=Me and $R^4$=4-Methylphenyl)

To a solution of 4-methylbenzaldehyde (12.6 g, 0.105 moles) in methanol (300 ml), ammonium hydroxide (sp. gr.=0.9, 180 ml) is added, followed by 2-hydroxyimino-1-dimethylamino-3-butanone hydrochloride (17.4 g, 0.0965 moles, described in Example 1). After standing overnight the mixture is evaporated to give a residue of the title compound. The residue is dissolved in methanol and a solution of hydrogen chloride in diethyl ether is added. The solution is treated with charcoal and filtered. The filtrate is evaporated and crystallized from methanol-diethyl ether to give the dihydrochloride salt of the title compound (23.99 g), mp 222°–224° C. Two recrystallizations from the latter solvent raised the melting point to 223°–226° C.; nmr (DMSO-$d_6$) δ 2.4(s), 2.52(s), 2.83(s), 4.6(s), 7.35(s), 8.2(s) and 12.2(broad); and anal. Calc'd. for $C_{14}H_{19}N_3O \cdot 2HCl$: C, 53.00; H, 6.62; N, 13.20% and Found: C, 52.55; H, 6.72; N, 13.34%.

In the same manner but replacing 4-methylbenzaldehyde with an equivalent amount of a following aldehyde of formula $R^4$—CHO: benzaldehyde, 4-fluorobenzaldehyde, 3-chlorobenzaldehyde, 2-methylbenzaldehyde, 2-hydroxybenzaldehyde, 3,4-dichlorobenzaldehyde, 2,6-dichlorobenzaldehyde, 2-furancarboxaldehyde, 3-thiophenecarboxaldehyde, 1-naphthalenecarboxaldehyde, 2-pyridinecarboxaldehyde, 2-methylpropanal, 4-chlorobenzaldehyde, 3,4,5-trimethylbenzaldehyde, 3-propylbenzaldehyde, 4-ethoxybenzaldehyde, 2,5-dimethoxybenzaldehyde, 4-trifluoromethylbenzaldehyde, acetaldehyde or hexanal, the following compounds of formula I are obtained, respectively: 1-hydroxy-N,N,4-trimethyl-2-phenyl-1H-imidazole-5-methanamine dihydrochloride, mp 213°–218° C., nmr(DMSO-$d_6$) δ 2.56(s), 2.88(s), 4.62(s), 7.6–8.3(m) and 12.3(broad) and anal. Calc'd. for $C_{13}H_{17}N_3O.2HCl$: C, 51.32; H, 6.26; N, 13.81% and Found: C, 50.97; H, 6.16; N, 13.86%; 2-(4-fluorophenyl)-1-hydroxy-N,N,4-trimethyl-1H-imidazole-5-methanamine dihydrochloride, mp, 243°–244° C., nmr(DMSO-$d_6$) δ 2.55(s), 2.88(s), 4.66(s), 7.65(m), 8.4(m) and 12.2(broad) and anal. Calc'd, for $C_{13}H_{16}FN_3O.2HCl$: C, 48.45; H, 5.63; N, 13.04% and Found: C, 48.60; H, 5.70; N, 13.18%; 2-(3-chlorophenyl)-1-hydroxy-N,N,4-trimethyl-1H-imidazole-5-methanamine dihydrochloride, mp 221°–223° C., nmr(DMSO-$d_6$) δ 2.5(s), 2.8(s), 4.5(s), 7.5–8.2(m) and 11.0 (broad) and anal. Calc'd. for $C_{13}H_{16}ClN_3O.2HCl$: C, 46.10; H, 5.36; N, 12.40% and Found: C, 46.82; H, 5.45; N, 12.85%; 1-hydroxy-N,N,4-trimethyl-2-(2-methylphenyl)-1H-imidazole-5-methanamine, mp 174°–175° C. (dec.), nmr(CDCl$_3$) δ 1.17(s), 2.0(s), 3.0(s), 7.1(m) and 14.2(s) and anal. Calc'd. for $C_{14}H_{19}N_3O$: C, 68.54; H, 7.81; N, 17.13% and Found: C, 68.13; H, 7.89; N, 16.18%; 2-[5-[(dimethylamino)methyl]-1-hydroxy-4-methyl-1H-imidazol-2-yl]phenol dihydrochloride, mp 220°–222° C., nmr(DMSO-$d_6$) δ 2.5(s), 2.84(s), 4.6(s), 6.9–7.95(m) and 11.5(broad) and anal. Calc'd. for $C_{13}H_{17}N_3O_2.2HCl$: C, 48.76; H, 5.98; N, 13.12% and Found: C, 48.82; H, 6.11; N, 13.22%; 2-(3,4-dichlorophenyl)-1-hydroxy-N,N,4-trimethyl-1H-imidazole-5-methanamine dihydrochloride, mp 232°–234° C., nmr(DMSO-$d_6$) δ 2.52(s), 2.85(s), 4.58(s), 7.85-8.6(m) and 9.6(broad) and anal. Calc'd. for $C_{13}H_{15}Cl_2N_3O.2HCl$: C, 41.85; H, 4.59; N, 11.26% and Found: C, 41.48; H, 4.60; N, 11.55%; 2-(2,6-dichlorophenyl)-1-hydroxy-N,N,4-trimethyl-1H-imidazole-5-methanamine hydrochloride, mp 224°–226° C., nmr(DMSO-$d_6$) δ 2.3(s), 2.7(s), 4.43(s), 7.76(s) and 9.0(broad) and anal. Calc'd. for $C_{13}H_{15}Cl_2N_3O.HCl$: C, 46.41; H, 4.79; N, 12.48% and Found: C, 45.21; H, 4.92; N, 12.35%; $H_2O$, 0.7%; 2-(2-furanyl)-1-hydroxy-N,N,4-trimethyl-1H-imidazole-5-methanamine dihydrochloride, mp 230°–233° C., nmr(DMSO-$d_6$) δ 2.5(s), 2.88(s), 4.6(s), 6.9(m), 7.6(m), 8.2(m) and 7.85(broad), anal. Calc'd. for $C_{11}H_{15}N_3O_2.2HCl$: C, 44.91; H, 5.79; N, 14.28% and Found: C, 43.59; H, 5.81; N, 14.29%; $H_2O$, 2.16%; 1-hydroxy-N,N,4-trimethyl-2-(3-thienyl)-1H-imidazole-5-methanamine dihydrochloride, mp 228°–230° C., nmr(DMSO-$d_6$) δ 2.5(s), 2.83(s), 4.6(s), 7.3–8.5(m) and 10.8(broad) and anal. Calc'd. for $C_{11}H_{15}N_3OS.2HCl$: C, 42.58; H, 5.53; N, 13.54% and Found: C, 41.80; H, 5.61; H, 13.86%; 1-hydroxy-N,N,4-trimethyl-2-(1-naphthalenyl)-1H-imidazole-5-methanamine maleate, mp 100°–125° C., nmr(DMSO-$d_6$) δ 2.24(s), 2.75(s), 4.22(s), 6.10(s), 7.35–8.25(m) and 9.8(broad) and anal. Calc'd. for $C_{17}H_{19}N_3O.C_4H_4O_4$: C, 63.46; H, 5.83; N, 10.58% and Found: C, 62.05; H, 5.92; N, 10.51%; 1-hydroxy-N,N,4-trimethyl-2-(2-pyridinyl)-1H-imidazole-5-methanamine hydrochloride, mp 140° C.(dec.), nmr(DMSO-$d_6$) δ 2.4(s), 2.8(s), 4.43(s), 7.4–9.0(m) and 10.2(broad) and anal. Calc'd. for $C_{12}H_{16}N_4O.HCl$; C. 53.62; H, 6.38; N, 20.85% and Found: C, 52.87; H, 6.39; H, 20.57%; 1-hydroxy-N,N,4-trimethyl-2-(1-methylethyl)-1H-imidazole-5-methanamine dihydrochloride, mp 208°–211° C., nmr(DMSO-$d_6$) δ 1.33(s), 1.45(s), 2.48(s), 2.81(s), 3.4(m) and 4.52(s) and anal. Calc'd. for $C_{10}H_{19}N_3O.2HCl$: C, 44.45; H, 7.83; N, 15.55% and Found: C, 44.47; H, 7.77; N, 15.41%; 2-(4-chlorophenyl)-1-hydroxy-N,N,4-trimethyl-1H-imidazole-5-methanamine dihydrochloride, mp 227°–228° C., nmr(DMSO-$d_6$) δ 2.54(s), 2.85(s), 4.63(s), 7.82(d), 8.32(d) and 9.1(broad) and anal. Calc'd. for $C_{13}H_{16}ClN_3O.2HCl.H_2O$: C, 43.77; H, 5.65; N, 11.78%; $H_2O$, 5.05% and Found: C, 43.97; H, 5.62; N, 11.93%; $H_2O$, 5.28%, 1-hydroxy-N,N,4-trimethyl-2-(3,4,5-trimethylphenyl)-1H-imidazole-5-methanamine; 1-hydroxy-N,N,4-trimethyl-2-(3-propylphenyl)-1H-imidazole-5-methanamine; 2-(4-ethoxyphenyl)-1-hydroxy-N,N,4-trimethyl-1H-imidazole-5-methanamine, 1-hydroxy-2-(2,5-dimethoxyphenyl)-N,N,4-trimethyl-1H-imidazole-5-methanamine, 2-(4-trifluoromethylphenyl)-1-hydroxy-N,N,4-trimethyl-1H-imidazole-5-methanamine; 1-hydroxy-N,N,2,4-tetramethyl-1H-imidazole-5-methanamine; and 1-hydroxy-N,N,4-trimethyl-2-pentyl-1H-imidazole-5-methanamine.

Similarily by replacing 1-dimethylamino-2-hydroxyimino-3-butanone hydrochloride with another compound of formula II described in Example I, the following compounds of formula I are obtained, respectively:

N,N-diethyl-1-hydroxy-4-methyl-2-(4-methylphenyl)-1H-imidazole-5-methanamine, 1-hydroxy-N,4-dimethyl-2-(4-methylphenyl)-N-pentyl-1H-imidazole-5-methanamine, N,N,4-triethyl-1-hydroxy-2-(4-methylphenyl)-1H-imidazole-5-methanamine, 1-hydroxy-4-(2-methylbutyl)-2-(4-methylphenyl)-N,N-dipropyl-1H-imidazole-5-methanamine and N-ethyl-1-hydroxy-2-(4-methylphenyl)-4-pentyl-N-propyl-1H-imidazole-5-methanamine.

EXAMPLE 3

3,5-Dihydroxyimino-1-Methyl-4-Piperidone Hydrochloride (II; $R^1$=Me and $R^2$ and $R^3$ together form a chain of formula —C(=NOH)—CH$_2$—)

Hydrogen chloride is introduced into a solution of 1-methyl-4-piperidone (14.3 g) in isopropanol (50 ml) at 0° C. until pH 3.5 is obtained. Isopropanol (2 ml) saturated with hydrogen chloride is added. To this solution, isopropyl nitrite (9.8 g) is added from a dropping funnel over 15 min at 20° C. The reaction mixture is stirred for 60 min at 35° C., diluted with 200 ml of diethyl ether and the crystalline material, mp 190°–196° C., 17.5 g, is collected by suction filtration. The crude product is triturated with 170 ml of hot acetonitrile and collected on a filter. The collected material is recrystallized from methanol-diethyl ether to obtain the title compound (12 g), mp 203°–204° C. [G. H. Cookson, J. Chem. Soc., 1328 (1953) reported mp 195° C. for the title compound].

EXAMPLE 4

6,7-Dihydro-1-Hydroxy-6-Methyl-2-Phenyl-1H-Imidazo[4,5-c]-Pyridine-4[5H]-One, Oxime (I; $R^1$=Me, $R^2$ and $R^3$ together form a chain of formula —C(=NOH)—CH$_2$— and $R^4$ is phenyl)

3,5-Dihydroxyimino-1-methyl-4-piperidone hydrochloride (6 g, described in Example 3) is added to a solution of benzaldehyde (2.6 g), 25% ammonium hydroxide (70 ml) and methanol (250 ml). The reaction mixture is stirred at room temperature for 15 hrs and evaporated. The residual aqueous solution is acidified with 5% hydrochloric acid and concentrated. The precipitate is collected by suction filtration, triturated with warm acetonitrile and recrystallized from aqueous acetonitrile to obtain the dihydrochloride salt of the title compound (5 g), mp 231°–233° C., nmr(trifluoroacetic acid) δ 3.49(s), 4.65(m), 5.1(m) and 7.6–8.3(m) and anal. Calc'd. for $C_{13}H_{14}N_4O_2 \cdot 2HCl$: C, 47.14%, H, 4.86; N, 16.91% and Found: C, 46.90; H, 4.75; N, 16.92%.

To obtain the title compound, the latter salt is dissolved in hot methanol, gaseous ammonia is introduced and the solution is concentrated. The crystalline material is filtered off and washed with water to obtain the title compound, mp 169°–170° C. When triturated with small amounts of boiing methanol and acetonitrile and dried, the title compound melts at 202°–203° C., nmr(DMSO-$d_6$) δ 2.44(s), 3.59(s), 7.40(m), 8.08(m) and 10.20 (broad).

In the same manner but replacing benzaldehyde with an equivalent amount of 4-chlorobenzaldehyde or pentanal, the following compounds of formula I are obtained, respectively: 2-(4-chlorophenyl)-6,7-dihydro-1-hydroxy-6-methyl-1H-imidazo[4,5-c]pyridine-4[5H]-one, oxime hydrochloride, mp 183°–184° C. and nmr(DMSO-$d_6$) δ 3.09(s), 4.49(s), 4.64(s), 7.61(d), 8.19(d) and 11.5(broad) and 2-butyl-6,7-dihydro-1-hydroxy-6-methyl-1H-imidazo[4,5-c]pyridine-4[5H]-one, oxime dihydrochloride.

We claim:

1. A compound of formula I

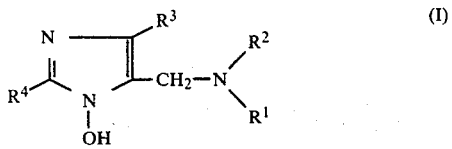

in which $R^1$, $R^2$ and $R^3$ each is lower alkyl, or $R^1$ is lower alkyl and $R^2$ and $R^3$ together form a chain of formula —C(=NOH)—CH$_2$— wherein the —CH$_2$— is joined to the nitrogen, and $R^4$ is lower alkyl, 1-naphthalenyl, 2-, 3- or 4-pyridinyl, 2- or 3-furyl, 2- or 3-thieny, phenyl or phenyl mono-, di- or trisubstituted with halo, lower alkyl, lower alkoxy, hydroxy, or trifluoromethyl, or a therapeutically acceptable acid addition salt thereof.

2. The compound of claim 1 in which $R^1$, $R^2$ and $R^3$ each is lower alkyl, and $R^4$ is lower alkyl, 1-naphthalenyl, 2-pyridinyl, 2-furyl, 3-thienyl, phenyl or phenyl mono or disubstituted with halo, lower alkyl or hydroxy, or a therapeutically acceptable acid addition salt thereof.

3. The compound of claim 1 in which $R^1$ is lower alkyl and $R^2$ and $R^3$ together form a chain of formula —C(=NOH)—CH$_2$— wherein the —CH$_2$— is joined to the nitrogen and $R^4$ is phenyl or phenyl mono- or disubstituted with halo or lower alkyl, or a therapeutically acceptable acid addition salt thereof.

4. 1-Hydroxy-N,N,4-trimethyl-2-(4-methylphenyl)-1H-imidazole-5-methanamine, as claimed in claim 1.

5. 1-Hydroxy-N,N,4-trimethyl-2-phenyl-1H-imidazole-5-methanamine, as claimed in claim 1.

6. 2-(4-Fluorophenyl)-1-hydroxy-N,N,4-trimethyl-1H-imidazole-5-methanamine, as claimed in claim 1.

7. 2-(3-Chlorophenyl)-1-hydroxy-N,N,4-trimethyl-1H-imidazole-5-methanamine, as claimed in claim 1.

8. 1-Hydroxy-N,N,4-trimethyl-2-(2-methylphenyl)-1H-imidazole-5-methanamine, as claimed in claim 1.

9. 2-[5-[(Dimethylamino)methyl]-1-hydroxy-4-methyl-1H-imidazole-2-yl]phenol, as claimed in claim 1.

10. 2-(3,4-Dichlorophenyl)-1-hydroxy-N,N,4-trimethyl-1H-imidazole-5-methanamine, as claimed in claim 1.

11. 2-(2,6-Dichlorophenyl)-1-hydroxy-N,N,4-trimethyl-1H-imidazole-5-methanamine, as claimed in claim 1.

12. 2-(2-Furanyl)-1-hydroxy-N,N,4-trimethyl-1H-imidazole-5-methanamine, as claimed in claim 1.

13. 1-Hydroxy-N,N,4-trimethyl-2-(3-thienyl)-1H-imidazole-5-methanamine, as claimed in claim 1.

14. 1-Hydroxy-N,N,4-trimethyl-2-(1-naphthalenyl)-1H-imidazole-5-methanamine, as claimed in claim 1.

15. 1-Hydroxy-N,N,4-trimethyl-2-(2-pyridinyl)-1H-imidazole-5-methanamine, as claimed in claim 1.

16. 1-Hydroxy-N,N,4-trimethyl-2-(1-methylethyl)-1H-imidazole-5-methanamine, as claimed in claim 1.

17. 2-(4-Chlorophenyl)-1-hydroxy-N,N,4-trimethyl-1H-imidazole-5-methanamine, as claimed in claim 1.

18. 6,7-Dihydro-1-hydroxy-6-methyl-2-phenyl-1H-imidazo[4,5-c]pyridine-4[5H]-one oxime, as claimed in claim 3.

19. A method of treating hypertension in a hypertensive mammal, which comprises administering to said mammal an effective antihypertensive amount of a compound of formula I, or a therapeutically acceptable acid addition salt thereof, as claimed in claim 1, 2 or 3.

20. A pharmaceutical composition, which comprises a compound of formula I, or a therapeutically acceptable acid addition salt thereof, as claimed in claim 1, 2 or 3, and a pharmaceutically acceptable carrier therefor.

21. A method of treating hypertension in a hypertensive mammal, which comprises administering to the mammal an antihypertensive effective amount of a compound of formula I of claim 1, or a therapeutically acceptable acid addition salt thereof, in combination with an effective amount of a diuretic and/or antihypertensive agent.

22. The method of claim 21 in which the agent is a diuretic thiazide, a mineralocorticoid antagonizing diuretic agent or a β-adrenergic blocking agent.

23. The method of claim 21 in which the agent is chlorothiazide, hydrochlorothiazide or propranolol.

24. The method of claim 21 in which the compound of formula I, or a therapeutically acceptable salt thereof, and the diuretic and/or antihypertensive agent is administered sequentially or simultaneously.

25. A pharmaceutical composition comprising a compound of formula I, or a therapeutically acceptable acid addition salt thereof, and a diuretic and/or antihypertensive agent.

26. The pharmaceutical composition of claim 25 in which the agent is a diuretic thiazide, a mineralocorticoid antagonizing diuretic agent or a β-adrenergic blocking agent.

27. The pharmaceutical composition of claim 25 in which the agent is chlorothiazide, hydrochlorothiazide or propranolol.

* * * * *